United States Patent [19]

Kim et al.

[11] Patent Number: 4,780,417
[45] Date of Patent: Oct. 25, 1988

[54] RAPID EXTRACTION, SEPARATION, AND DETECTION METHOD FOR A SEPARATE ANALYSIS OF FREE AND TOTAL SULFITES IN FOODS BY ION CHROMATOGRAPHY

[75] Inventors: Hie-Joon Kim; Young-Kyung Kim, both of Wayland, Mass.

[73] Assignee: The United States of America as represented by the Secretary of the Army, Washington, D.C.

[21] Appl. No.: 19,082

[22] Filed: Feb. 25, 1987

[51] Int. Cl.$^4$ ............................................. G01N 33/02
[52] U.S. Cl. .................................... 436/20; 436/102; 436/121; 436/123
[58] Field of Search ................. 436/20, 102, 123, 119, 436/150, 151, 161, 178, 121; 210/639

[56] References Cited

U.S. PATENT DOCUMENTS

| | | | |
|---|---|---|---|
| 3,920,397 | 11/1975 | Small et al. | 436/119 X |
| 4,036,704 | 7/1977 | Takata | 436/119 X |
| 4,272,246 | 6/1981 | Fritz et al. | 436/119 X |
| 4,666,856 | 5/1987 | Irgum et al. | 436/178 X |

FOREIGN PATENT DOCUMENTS

970216  10/1982  U.S.S.R. ................................ 436/20

OTHER PUBLICATIONS

Sullivan et al., Jul. 1985, "Food Tech.", p. 45.
"Chemistry of Sulphur Dioxide in Foods", Elsevier Applied Sci. Pub., New York 1984, B. L. Wedzicha, pp. 142–143.
Cooper et al., "Ion Chromatography for Determining Residual Sulfite on Shrimp", J. of Food Sci., vol. 51, No. 4, pp. 924–929, 1986.
Anderson et al., "Ion Chromatographic Determination of Sulfites in Foods", J. Assoc. Off. Anal. Chem., vol. 69, No. 1, pp. 14–19, 1986.

*Primary Examiner*—Benoit Castel
*Assistant Examiner*—Timothy M. McMahon
*Attorney, Agent, or Firm*—Lawrence E. Labadini; Robert P. Gibson

[57] ABSTRACT

A process for the rapid extraction, separation, and detection of free and total sulfites in food is disclosed. The process comprises the steps of (a) extracting sulfites from a sample in the presence of a medium having a selected pH to produce an extractant; (b) filtering the extractant; (c) subjecting the filtered extractant to anion exclusion chromatography to produce a sulfite-containing effluent; and (d) detecting the proportion of sulfites in the effluent. The process may be used either to determine free sulfites (by performing extraction in the presence of an acid medium), or to determine total sulfites (by performing extraction in the presence of an alkaline medium). The process of the present invention may be used to determine sulfite levels of 1.0 ppm or less.

11 Claims, 1 Drawing Sheet

FIGURE
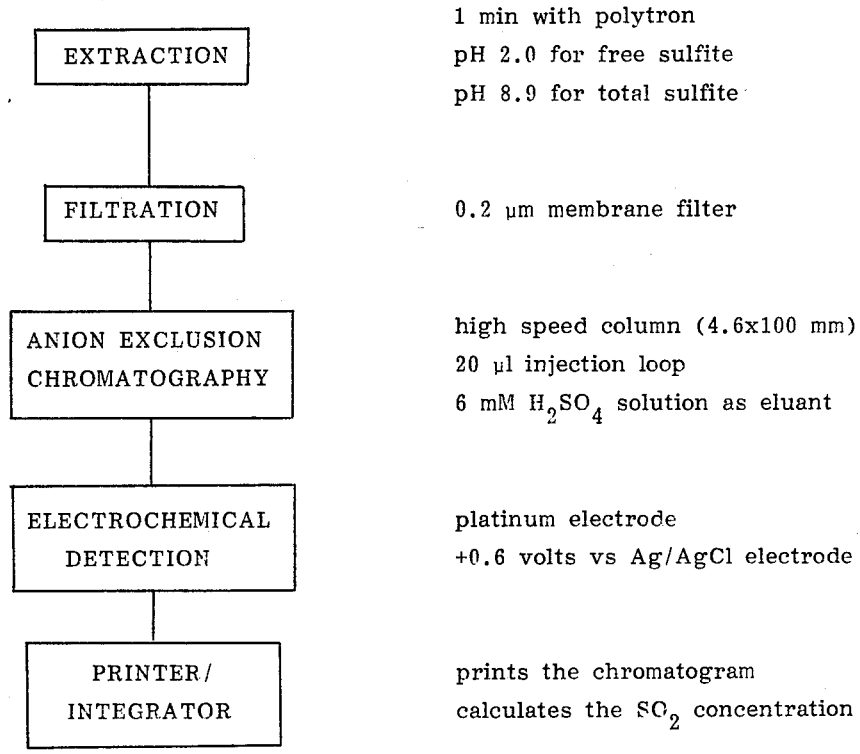

RAPID EXTRACTION, SEPARATION, AND DETECTION METHOD FOR A SEPARATE ANALYSIS OF FREE AND TOTAL SULFITES IN FOODS BY ION CHROMATOGRAPHY

BACKGROUND OF THE INVENTION

The invention described herein may be manufactured, used and licensed by or for the Government for Governmental purposes without the payment to us of any royalties thereon.

FIELD OF THE INVENTION

Sulfiting agents are widely used in the food industry for various reasons. One major role of sulfites in food is for the prevention of enzymatic browning in fresh fruits and vegetables. A second use is for the control of nonezymatic browning in processed foods.

However, recent concern over levels of sulfites in food has become a matter of concern inasmuch as many persons display a hypersensitive reaction to sulfites in food. Therefore, the FDA has published regulations regarding use of sulfites in food. The new regulatons, which were published on July 9, 1986, require that the presence of sulfiting agents in foods above the level of 10 ppm be declared, effective Jan. 9, 1987, whether they have been added directly or indirectly via the ingredients of the food. A common source of an indirect addition of a sulfite is dehydrated fruits or vegetables such as dehydrated potatoes, onions, garlic, peas, celery, pepper, apple, banana, avocado, or syrup. Thus, foods containing any of these ingredients, such as instant soup, gravy mix, guacamole mix, breakfast cereals, or salad dressing, need to declare on their labels whether a sulfite level in excess of 10 ppm exists.

Thus, a need exists in the art for an analytical technique which is reliable at the level of 10 ppm or less of sulfites.

One commonly used method for analyzing the amount of sulfites in food is the modified Monier-Williams method. This method comprises removal of sulfites from a food matrix by distillation in strong acid and detection by titration with alkali after oxidation of sulfur dioxide to sulfuric acid in $H_2O_2$. However, this method possesses various deficiencies: for one, the method requires distillation for about 1.75 hours, making the method relatively time consuming. Furthermore, the Monier-Williams method has an inherent deficiency in that some volatile materials, such as acetic acid or sulfur compounds, tend to co-distill with sulfur dioxide. Also, this method lacks specificity because titration with alkali measures the total acidity in the trapping solution but not necessarily the sulfuric acid derived from sulfite. In other words, the Monier-Williams method is subject to interference at low sulfite levels.

Recently, ion chromatographic methods for analysis of sulfites in food have received much attention in the art. In most of these approaches, ion exchange chromatography is used to separate sulfite from other interfering compounds in a distillate and to improve the sensitivity of detection. Examples of such methods are disclosed in Sullivan, D. M. and Smith, R. L. 1985, "Determination of Sulfite in Foods by Ion Chromatography", *Food Technology*, 39: 45; Anderson, C., Warner, C. R., Daniels, D. H., and Padgett, K. L. 1986, "Ion Chromatographic Determination of Sulfites in Foods", *J. Assoc. Off. Anal. Chem.*, 69: 14; and Cooper, P. L., Marshall, M. R., Gregory III, J. F., and Otwell, W. S. 1986, "Ion Chromatography for Determining Residual Sulfite in Shrimp", *J. Food Sci.*, 51 (4): 924. However, each of these methods involves the time consuming process of distillation inherent in the Monier-Williams process. Furthermore, the prior art methods do not distinguish between levels of free versus total (i.e., free plus bound) sulfites in food, a significant deficiency inasmuch as hypersensitive reactions in affected individuals are probably to free rather than bound sulfites.

SUMMARY OF THE INVENTION

Accordingly, an extremely fast, sensitive, reliable and easy-to-use analytical technique for separate determination of free and total sulfites in food has been developed. The present invention comprises a process for analysis of sulfites in a food sample comprising the steps of: (a) extending sulfites from the sample in the presence of a medium having a selected pH to produce an extractant: (b) filtering the extractant; (c) subjecting the filtered extractant to anion exclusion chromatography to produce a sulfite-containing effluent; and (d) detecting the proportion of sulfites in the effluent. Free sulfites may be analyzed by extraction of the food sample in the presence of an acid medium; total sulfites, by extraction of the food sample in the presence of an alkaline medium.

In preferred embodiments, the anion exclusion chromatography step is performed in a high-speed column of sulfonated polystyrene divinylbenzene, in the presence of an acidic solution as eluant.

In another preferred embodiment, the detection step (d) is an electrochemical detection step and is performed using a platinum working electrode and an Ag-/AgCl reference electrode.

In still another preferred embodiment, an additional step (e) comprises using a printer/integrator to print the chromatogram and calculate the sulfite concentration.

BRIEF DESCRIPTION OF THE DRAWING FIGURE

The drawing FIGURE is a schematic representation of the preferred embodiment of the present invention.

DETAILED DESCRIPTION OF THE INVENTION

As discussed above, the present invention is a process for the analysis of sulfites in a food sample comprising the steps of (a) extracting sulfites from the sample in the presence of a medium having a selected pH to produce an extractant; (b) filtering the extractant; (c) subjecting the filtered extractant to anion exclusion chromatography to produce a sulfite-containing effluent; and (d) detecting the proportion of sulfites in the effluent.

The first essential step of the process comprises extracting sulfites from the sample. It is this step which allows for separate measurement of free and total (i.e., free plus bound) sulfites in a sample. When it is desired to extract free sulfites, an acidic medium is used; if total sulfites are to be extracted, an alkaline medium is used.

By an acidic extraction medium is meant a medium having a pH of from about 1.0 to about 3.0 and preferably about pH 2.0. The acidic medium may be an aqueous solution of any strong acid having a concentration of greater than about 5 mM. A preferred acidic extractant is 6 mM $H_2SO_4$ having a pH of 2.0.

By an alkaline extraction medium is meant a medium having a pH of from about 8.0 to about 10.0, and preferably about a pH of 8.9. A preferred alkaline medium is a 20 mM sodium phosphate buffer, having a pH of about 8.9.

D-mannitol may be added to either extraction medium. Addition of D-mannitol to the medium minimizes oxidative loss of sulfite, thus improving the precision of the method. In the method of the present invention, a precision level corresponding to a coefficient of variation of approximately 4% may be achieved.

The extraction is performed by rapid homogenization, i.e., in less than about one minute. A preferred homogenization apparatus is the Polytron high-speed homogenizer (Brinkmann Instruments Company, Westbury, N.Y.). The homogenizer can be reused for successive analyses of multiple samples after a brief washing, e.g., by running with water for up to about one minute. This represents a distinct advantage over prior art distillation methods, wherein the distillation and trapping apparatus need be washed and reassembled after each analysis, which therefore made these methods unsuitable for multiple sample analysis.

The next essential step is a filtration step wherein the extractant from the previous step is run through a membrane filter. Any filter which is capable of selectively removing water insoluble materials such as cellulose and other residue is suitable for this purpose. A membrane filter having a pore size of between about 0.2 and 1.0 μm may be used. A preferred type of filter is a 0.2 μm membrane filter such as a Millex-GV 0.2 μm filter unit (Millpore Corp., Bedford, Mass.)

The next essential step of the process is an anion exclusion chromatography step. Ion exclusion chromatography is a known separation process which is discussed in Remington's Pharmaceutical Sciences, Fifteen Edition, 1975, p. 624, incorporated herein by reference. This process utilizes a stationary phase exchange making use of an ion-exchange resin, but which operates under conditions wherein the compound or compounds to be separated have the same charge as the resin and therefore do not exchange with it. In ion-exchange, the resin and ionized compounds have the opposite charge so that ionized species are retarded; under ion exclusion conditions, ionized materials are eluted first because they are partially excluded by ionic repulsion from the internal liquid of the resin matrix.

An accepted theory as to how separation occurs in ion exclusion chromatography is disclosed in U.S. Pat. No. 4,314,823 to Rich, Jr. et al., incorporated herein by reference. According to this theory, the network of the resin serves as a boundary, which behaves as a semipermeable membrane, between the interstitial liquid between the resin particles and the occluded liquid inside the resin. Due to Donnan exclusion, highly ionized molecules, such as strong mineral acids, are excluded from the resin particles and passed directly through the column in the void volumn peak. Weakly ionic molecules may enter the resin phase in acid form and are retained by the resin for later elution than strong acids. Weak acids and their salts are readily separated from strong acids and their salts on the separation column in this manner.

In general, the weak acids in their molecular non-ionized form can penetrate into the interior of the ion exchange resin while the strong highly ionized acids are excluded. By using an ion exchange resin in hydrogen ion form, salts of weak acids which are highly ionized (e.g., of alkali metals) are converted to their acid form which may be retained by the column. The above discussion of ion exclusion chromatography applies in an analogous manner to the separation of cations, except, in this case, an anion exchange resin in the hydroxide form is used in the ion exclusion column.

A preferred anion exclusion apparatus which may be used in the process of the present invention is a high-speed anion exclusion column, such as the Wescan ion chromatography system (Santa Clara, CA).

The resin employed in the ion exclusion column is of a type in which the dominant retentive force is penetration of the weak acid in molecular form into the interior of the resin for retention therein for a time until elution in the eluant stream in inverse order to such retention forces. This effect dominates over any ion exchange effect. To permit this to occur, the pore size of the resin should be relatively large to permit penetration of such molecules.

A preferred substrate of this type is a surface sulfonated copolymer of styrene and divinylbenzene having about 1 to 8% divinylbenzene cross-linking.

The filtrate which results from step (b) of the process is injected into the chromatograph at an injection volume of about 20 μl to about 100 μl and preferably about 100 μl into the chromatograph and is eluted with an acidic solution (eluant) which preferably has a concentration greater than 5 mM, i.e., 5 mM to 20 mM. Preferably the eluant is 6 mM $H_2SO_4$. It has been found that if an eluant more dilute than 6 mM is employed, poor separation of sulfite from ascorbic acid results. The elution preferably proceeds at a flow rate of about 0.5 to about 1.0 ml/min and preferably at about 0.6 ml/min.

The third essential step of the present invention involves detection of the proportion of sulfites contained in the effluent resulting from the chromatography step. Preferably, the detection step is by electrochemical means.

The electrochemical detection step may be performed by any apparatus capable of detecting only compounds which are oxidizable at the applied voltage at the pH of the effluent. The voltage may be between about 0.40 volts and 0.60 volts. A suitable electrochemical detector is one having a platinum working electrode which is set at +0.6 volts and using an Ag/AgCl reference electrode.

An optional step of the process comprises using a printer/integrator which is capable of interpreting the output of the electrochemical detector. A suitable computing integrator is a Spectra-Physics (San Jose, CA) SP4200 Computing Integrator. The printer/integrator is capable of reading and printing the output of the detector and calculating the area under the curve to calculate sulfite concentration.

A further disclosure of the nature of the present invention is provided by the specific examples of the practice of the invention. It should be understood that the data disclosed serve only as examples and are not intended to limit the scope of the invention.

EXAMPLES 1-6

Free sulfites were extracted from samples of three dehydrated foods: freeze-dried pears from military ration, Meal, Ready-to-Eat (MRE), (Innovative Foods, Inc., South San Francisco, Calif.) (Example 1); instant mashed potatoes from Basic American Foods, BAF, San Francisco, Calif. (Example 2); and freeze-dried green bell peppers from California Vegetable Concentrate CVC, Modesto, Calif. (Example 3).

From 0.1 to 0.3 grams of each sample were solubilized in 30 ml 5 mM $H_2SO_4$, 10 mM D-mannitol solution (pH 2.0) by homogenizing at high speed with a Polytron homogenizer (Brinkmann Instrument Company, Westbury, N.Y.) for one minute.

Total sulfites were similarly extracted from a separate set of three dehydrated samples with 30 ml 20 mM $Na_2HPO_4$, 10 mM D-mannitol solution (pH 8.9) (Examples 4-6, respectively).

The extract in each case was filtered through a Millex-GV 0.2 μm filter units (Millipore Corp., Bedford, Mass.) for ion chromatography. All solutions for extraction and chromatography were degassed under vacuum before use.

A Wescan ion chromatography system (Santa Clara, Calif.) equipped with anion exclusion column (30×7.8 mm), Ion-Guard anion exclusion cartridge, conductivity detector, electrochemical detector, and Spectra-Physics (San Jose, Calif.) SP 4200 computing integrator was used for sulfite analysis. Standard solutions corresponding to 2.0, 4.0, and 6.0 ppm $SO_2$ were prepared with sodium metabisulfite ($Na_2S_2O_5$) in the pH 2.0 and 8.9 extraction solutions. The standard solutions in the filtrate made from food solutions in the preceding step were immediately injected (injected volume=100 μm) into the chromatograph and eluted with 5 mM $H_2SO_4$ solution (pH 2.0) at a flow rate of 0.6 ml/min. The electrochemical detector with platinum working electrode was set at +0.40 volts vs Ag/AgCl reference electrode. The output from the detector was fed to the computing integrator, which gave the area under the curve used in calculating sulfite concentrations. A summary of free and total sulfites in the three samples corresponding to Examples 1-6 is shown in the following table.

TABLE I

| Sample | Example No. | Free $SO_2$, ppm | Example No. | Total $SO_2$, ppm | Free/Total, Ratio |
|---|---|---|---|---|---|
| Freeze-dried green pepper[a] | 1 | 524 ± 58 | 4 | 1,796 ± 200 | 0.29 |
| Instant mashed potatoes[a] | 2 | 366 ± 28 | 5 | 536 ± 22 | 0.68 |
| Freeze-dried pears[b] | 3 | 239 ± 24 | 6 | 509 ± 23 | 0.47 |

[a]Average of three determinations on same lot
[b]Average of single determination on three different lots

EXAMPLES 7-42

The process of Examples 1-6 was substantially followed for eighteen items except that (1) a Brownlee Polypore H sulfonated polystyrene/divinylbenzene, 4.6×100 mm was used as the anion exclusion material; and (2) a 6 mM $H_2SO_4$ solution was used as eluant. In Examples 7-24, an acidic medium (sulfuric acid, pH 2.0) was used in the extraction of free sulfites; in Examples 25-42, an alkaline medium (sodium phosphate, pH 8.9) for the extraction of total sulfites. The results of the analyses are given below in Table II.

TABLE II

| Sample | Example No. | Free $SO_2$, ppm[a] | Example No. | Total $SO_2$, ppm[a] |
|---|---|---|---|---|
| Freeze-dried green bell pepper dice | 7 | 1747 | 25 | 5819[b] |
| Freeze-dried chopped celery | 8 | 320 | 26 | 517 |
| Freeze-dried peas | 9 | 47 | 27 | 345 |
| Freeze-dried cauliflower | 10 | 0 | 28 | 0 |
| Mixed dried fruits | 11 | 99 | 29 | 1827 |
| Golden raisin | 12 | 95 | 30 | 1555 |
| Instant mashed potatoes | 13 | 219 | 31 | 488 |
| Hash Brown Potatoes | 14 | 61 | 32 | 347 |
| Dip-treated lettuce[b] | 15 | 380 | 33 | 536 |
| Pepper in vinegar | 16 | 184 | 34 | 307 |
| Cocktail onion | 17 | 8.7 | 35 | 64.1 |
| Lemon juice | 18 | 174 | 36 | 278 |
| Lime juice | 19 | 135 | 37 | 218 |
| Wine vinegar | 20 | 3.3 | 38 | 48.4 |
| Red wine, A | 21 | 32 | 39 | 163 |
| Red wine, B | 22 | 10 | 40 | 156 |
| Beer | 23 | <0.5 | 41 | <0.5 |
| Flaked Coconut | 24 | <0.5 | 42 | 9.8 |

[a]Average of duplicate measurements.
[b]Cut ¼" × ¼", dipped in ⅛ oz/gal sodium metabisulfite solution for 1 min, and drained.

EXAMPLES 43-50 AND COMPARATIVE EXAMPLES 1-8

The process of Examples 7-42 was substantially followed for eight items (Examples 43-50). The results of total (free and bound) sulfite analysis are given below. The process of Monier-Williams (discussed above) was also conducted on each of the eight items of Examples 43-50 (Comparative Examples 1-8). The results of the two analyses are compared side-by-side in Table III below:

TABLE III

| | Method of Present Invention[a] | | Monier-Williams Method[a] | |
|---|---|---|---|---|
| Sample | Total Example No. | Total $SO_2$, ppm | Comparative Example No. | Total $SO_2$, ppm |
| Golden Raisin | 43 | 1555 | 1 | 1601 |
| Instant Mashed Potatoes | 44 | 488 | 2 | 390 |
| Lemon Juice | 45 | 278 | 3 | 255 |
| Dip-treated Shrimp | 46 | 268 | 4 | 231 |
| Wine Vinegar | 47 | 48 | 5 | 116[b] 49[c] |
| Instant Vegetable Soup | 48 | 43 | 6 | 41 |
| Flaked Coconut | 49 | 9.8 | 7 | 11.1 |
| Beer | 50 | <0.5 | 8 | 0.9 |

[a]Average of duplicate measurements
[b]Uncorrected
[c]Corrected for acetic acid

CONCLUSION

The present invention provides a process for the rapid extraction, separation, and detection of free and total sulfites in food. Unlike prior art processes, the present process is highly sensitive in its ability to measure small amounts of sulfites in food, i.e., it is capable of detecting sulfite levels of 1.0 ppm or lower. Further, it is capable of measuring free and total sulfite levels separately. Additionally, the method of the present invention is fast, continuous and convenient relative to prior art processes. Finally, as can be seen from the numerous Examples shown hereinabove, the process of the present invention is highly versatile as shown by the variety of foods which may be tested thereby.

While the invention has been disclosed in this patent application by reference to the details of the preferred embodiments of the invention, it will be understood that this disclosure is intended in an illustrative rather than a limiting sense, as it is contemplated that modifications will readily occur to those skilled in the art, within the spirit of the invention and the scope of the appended claims.

What is claimed is:

1. A process for analysis of sulfites in a food sample comprising the steps of:
    (a) extracting sulfites from such a sample in the presence of a aqueous medium having a selected pH to produce an extractant of sulfites;
    (b) filtering said extractant to remove water insoluble materials;
    (c) subjecting said filtered extractant to anion exclusion chromatography to produce a sulfite-containing effluent; and
    (d) detecting electrochemically the concentration of sulfites in said effluent.

2. The process of claim 1 wherein said anion exclusion chromatography step (c) is performed in a column containing sulfonated polystyrene/divinylbenzene.

3. The process of claim 1 additionally comprising a step (e) wherein a printer/integrator is used to print the chromatogram and calculate sulfite concentration.

4. The process of claim 1 wherein said extraction step (a) is performed at an alkaline pH of from about 8.0 to 10.0 to extract total sulfites.

5. The process of claim 4 wherein said alkaline pH is about 8.9.

6. The process of claim 1 wherein said extraction step (a) is performed at an acid pH of from about 1.0 to 3.0 to extract free sulfites.

7. The process of claim 6 wherein said acid pH is about 2.0.

8. The process of claim 1 wherein said anion exclusion chromatography step (c) is performed with an acidic solution as eluant.

9. The process of claim 8 wherein the eluant has a concentration from 5 mM to 20 mM $H_2SO_4$.

10. The process of claim 1 wherein said detection step is performed by detection means capable of detecting only compounds which are oxidizable at the applied voltage at the pH of the effluent.

11. The process of claim 10 wherein said detection means has a platinum working electrode and an Ag-/AgCl reference electrode and said applied voltage is between 0.40 and 0.60 volts.

* * * * *